United States Patent
Nagao et al.

(10) Patent No.: US 6,403,625 B1
(45) Date of Patent: Jun. 11, 2002

(54) FLUORESCENT LABELING REAGENTS

(75) Inventors: Yoshimitsu Nagao; Susumu Ito, both of Tokushima (JP)

(73) Assignee: Daiichi Pure Chemicals Co., Ltd., Tokyo (JP)

(*) Notice: Subject to any disclaimer, the term of this patent is extended or adjusted under 35 U.S.C. 154(b) by 0 days.

(21) Appl. No.: 09/762,305

(22) PCT Filed: Aug. 12, 1999

(86) PCT No.: PCT/JP99/04382

§ 371 (c)(1),
(2), (4) Date: May 3, 2001

(87) PCT Pub. No.: WO00/09502

PCT Pub. Date: Feb. 24, 2000

(30) Foreign Application Priority Data

Aug. 12, 1998 (JP) ............................................. 10-228241

(51) Int. Cl.$^7$ ..................... C07D 417/14; A61K 31/425

(52) U.S. Cl. .................. 514/369; 548/181; 424/9.6

(58) Field of Search .................. 548/181; 514/369; 424/9.6

(56) References Cited

U.S. PATENT DOCUMENTS

| | | |
|---|---|---|
| 2,895,955 A | 7/1959 | Heseltine et al. |
| 5,750,722 A | 5/1998 | Huynh et al. |

FOREIGN PATENT DOCUMENTS

| | | |
|---|---|---|
| JP | 7-33657 | 2/1995 |
| JP | 9505558 | 6/1997 |
| JP | 9309845 | 12/1997 |

OTHER PUBLICATIONS

Terukage Hirata et al., "Synthesis and Reactivities of 3–Indocyanine–green–acyl–1, 3–thiazolidine–2–thione(ICG–ATT) as a New Near–Infrared Flourescent–Labeling Reagant", Bioorganic & Medicinal Chemistry, vol. 6, pp. 2179–2184 (1998).

Gabor Patonay et al., "Near–Infrared Flourogenic Labels: New Approach to an Old Problem", Analytical Chemistry, vol. 63, No. 6, pp. 321A–327A (1991).

Philip L. Southwick et al., "Cyanine Dye Labeling Reagents–Carboxymethylindocyanine Succinimidyl Esters", Cytometry vol. 11 pp. 418–430 (1990).

Yoshimitsu Nagao et al., "A New Practical Synthetic Method:Monitored Aminolysis of 3–Acyl–1, 3–thiazolidine–2–thione", Heterocycles, vol. 17, pp. 537–554 (1982).

Silvio Folli et al., "Antibody–Indocyanin Conjugates for Immunophotodetection of Human Squamous Cell Carcinoma in Nude Mice", Cancer Research, vol. 54, pp. 2643–2649, (1994).

An English Language abstract of JP 9–309845.

Kaoru Sajatabu, M.D., D.M.Sc. et al., "Noninvasive Optical Imaging of the Subarachnoid Space and Cerebrospinal Fluid Pathways Based on Near–Infrared Fluorescence", J. Neurosurg., vol. 87, pp. 738–745 (1997).

Lauren A. Ernst et al., "Cyanine Dye Labeling Reagents for Sulfhydryl Groups", Cytometry, vol. 10, pp. 3–10 (1989).

Ratnakar B. Mujumdar et al., "Cyanine Dye Labeling Reagents Containing Isothiocyanate Groups", Cytometry, vol. 10, pp. 11–19 (1989).

Ratnakar B. Mujumdar et al., "Cyanine Dye Labeling Reagents: Sulfoindocyanine Succinimidyl Esters", Bioconjugate Chemistry, vol. 4, No. 2, pp. 105–111 (1993).

Susmu Ito et al., "Development of Fluorescence–Emitting Antibody Labeling Substance by Near–Infrared Ray Excitation", Bioorganic & Medicinal Chemistry Letter, vol. 5, No. 22, pp. 2689–2694 (1995).

Yoshimitsu Nagao et al., "Peptide–Bond Formation, Chemoselective Acylation of Amino Acids, and Crosslinking Reaction Between Amino Acids Utilizing a Functional Five–Membered Heterocycle, 1,3–Thiazolidine–2–thione", J. Chem. Soc., Perkin Trans., pp. 2439–2446 (1984).

Kaoru Skatani et al., "Near Infrared Imaging of Indocyanine Green Distributed in Biological Tissues—Possibility of Non–Non–Contacting Reflecting Imaging–", Medical Electron and Bioengineering (Iyodenshi to Seitaikogaku), vol. 34, pp. 316–322, (1996), accompanied by an English language abstract.

Yoshimitsu Nagao et al., "A New Practical Synthetic Method: Monitored Aminolysis of 3–Acyl–1, 3–Thiazolidine–2–Thione", Heterocycles, vol. 17, pp. 537–541 and 544–554 (1982).

(List continued on next page.)

*Primary Examiner*—Robert Gerstl
(74) *Attorney, Agent, or Firm*—Greenblum & Bernstein, P.L.C.

(57) ABSTRACT

Compounds represented by the following formula (I),:

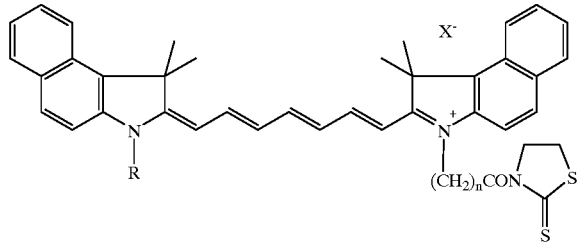

wherein R represents a lower alkyl group which may be substituted; n represents an integer of from 1 to 10; and X represents an anion species. The compounds are useful as active ingredients of fluorescent labeling agents or medicaments for diagnosis.

6 Claims, No Drawings

OTHER PUBLICATIONS

Takuya Hayashi et al., "Enhanced Diode Laser Ablation Using Submucosal Injection of Indocyanine Green Solution: Part I; Irradiation to the Resected Porcine Gastric Walls and Canine Gastric Walls Under Laparotomy", *Gastroenterological Endoscopy*, vol. 39, No. 10, pp. 1753–1765 (1997), accompanied by an English language abstract.

Takuya Hayashi et al., "Enhanced Diode Laser Ablation Using Submucosal Injection of Indocyanine Green Solution: Part II; –Endoscopic Irradiation to the Canine Stomach–", *Gastroenterological Endoscopy*, vol. 39, No. 10, pp. 1766–1774 (1997), accompanied by an English language abstract.

Terukage Hirata et al., "Synthesis and Reactivities of 3–Indocyanine–green–acyl–1,3–thiazolidine–2–thione (ICG–ATT) as a New Near–Infrared Fluorescent–labeling Reagent", Bioorg. Med. Chem., vol. 6, No. 11, pp. 2179–2184 (1998).

FLUORESCENT LABELING REAGENTS

TECHNICAL FIELD

The present invention relates to 3-indocyanine green-acyl-1,3-thiazolidine-2-thiones useful for fluorescent labeling agents and the like.

BACKGROUND ART

Polymethyne dyes absorb light in the near infrared region (600 to 1200 nm) and emit fluorescence (Patonay, G. et al., Anal. Chem., 1991, 63, 321A). They are characterized by high molecular absorbance and very high fluorescent emission. One of these dyes, indocyanine green (ICG) (U.S. Pat. No. 2,895,955; 1959), has an excellent feature of extremely low interference by absorption scattering in the near infrared region and fluorescence of a molecule in a living body, and has been clinically used for diagnosis of liver functions. Accordingly, derivatives of the aforementioned fluorescent compound are expected to be useful as fluorescent labeling agents.

It has been known that proteins such as bovine serum albumin (BSA) and immunoglobulin G (IgG) can be labeled with fluorescence by using the aforementioned fluorescent compound per se or its derivative (Southwick P. L. et al., Cytometry, 1990, 11, 418; Ernst, L. A. et al., Cytometry, 1989, 10, 3; Mujumdar, R. B. et al., Cytometry, 1989, 10, 11; Mujumdar, R. B. et al., Bioconjugate Chem., 1933, 4, 105; Ito, S. et al., Bioorg. Med. Chem. Let., 1995, 5, 2689). In these reports, it is explained that a protein labeled with fluorescence can be used for ultramicroanalysis by fluorescence measurement (Mujumdar, R. B. et al., Bioconjugate Chem., 1933, 4, 105), and that the protein can be a diagnostic reagent for very small stomach cancers (Ito, S. et al., Bioorg. Med. Chem. Let., 1995, 5, 2689).

Nagao et al. elucidated some features in aminolysis of various 3-acyl-1,3-thiazolidine-2-thione (ATT) derivatives by utilizing active amide structures, and reported that the ATT moiety selectively reacts with an amino group (Nagao, Y. et al., J. Chem. Soc., Perkin Trans., 1, 1984, 2439; Nagao, Y. et al., Heterocycles, 1982, 17, 537).

DISCLOSURE OF THE INVENTION

An object of the present invention is to provide novel compounds useful as fluorescent labeling agents. In particular, the object of the present invention is to provide compounds which have high fluorescence intensity in the near infrared region and can function to group-selectively and efficiently label proteins and oligopeptide compounds. The inventors of the present invention made intensive studies to achieve the aforementioned objects. As a result, they found that indocyanine green amide derivatives of 1,3-thiazolidine-2-thione have the aforementioned features and are extremely useful as fluorescent labeling agents. The present invention was achieved on the basis of the above findings.

The present invention thus provides compounds represented by the following formula (I):

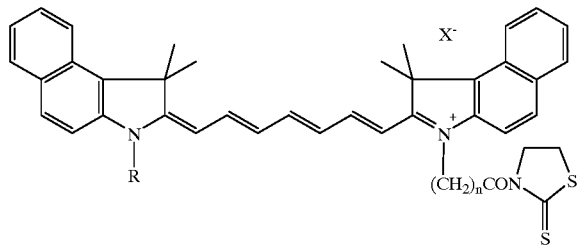

wherein R represents a lower alkyl group which may be substituted; n represents an integer of from 1 to 10; and X represents an anion species. According to preferred embodiments of this invention, there are provided the aforementioned compounds wherein R is a $C_{1-6}$ alkyl group which may have one sulfonic acid group, and n is an integer of from 4 to 6; the aforementioned compounds wherein R is a $C_{1-6}$ alkyl group, and n is 5; and the aforementioned compound wherein R is ethyl group, and n is 5. As a preferred embodiment of this invention, there is provided 2-[7-(1,3-dihydro-1,1-dimethyl-3-ethylbenz[e]indolin-2-ylidene)-1,3,5-heptatrienyl]-1,1-dimethyl-3-[[6-[(1,3-thiazolidine-2-thion)-1-yl]-6-oxo]hexyl]-1H-benz[e]indolium chloride.

According to another aspect of the present invention, there are provided a fluorescent labeling agent which comprises the compound represented by the aforementioned formula (I); a medicament for diagnosis which comprises the compound represented by the aforementioned formula (I), and is preferably used for fluorescence imaging method; and a medicament which comprises the compound represented by the aforementioned formula (I) and is preferably used for cancer treatment by using a laser, more preferably for endoscopic cancer treatment by using a near infrared laser.

According to a further aspect of the present invention, there are provided a use of the compound represented by the aforementioned formula (I) for the manufacture of the aforementioned medicament; a method of immunochemical staining of a living tissue by using the compound represented by the aforementioned formula (I); a method for diagnosis by fluorescence imaging method with the compound represented by the aforementioned formula (I), preferably a method for diagnosis of a cancer; and a method for endoscopic treatment of a cancer with a laser, preferably a near infrared laser, by using the compound represented by the aforementioned formula (I).

BEST MODE FOR CARRYING OUT THE INVENTION

In the aforementioned formula (I), R represents a lower alkyl group which may be substituted; n represents an integer of from 1 to 10; and X represents an anion species. As the lower alkyl group, a straight chain or branched chain alkyl group having carbon atoms of from 1 to about 6 can be used. More specifically, methyl group, ethyl group, n-propyl group, isopropyl group, n-butyl group, sec-butyl group, tert-butyl group or the like can be used. The symbol "n" is preferably an integer of from 4 to 6, more preferably 5. The kind of X is not particularly limited. For example, as an monovalent anion species, a halogen ion such as chlorine ion, bromine ion, or iodine ion can be used.

When the lower alkyl group represented by R has substituents, the number, the kind, and the position of the substituents are not particularly limited, and examples of the substituents include sulfonic acid group, hydroxyl group, carboxyl group, halogen atoms (may be any of fluorine atom, chlorine atom, bromine atom, or iodine atom), lower alkoxyl groups (e.g., methoxy group, ethoxy group and the like), amino group, mono- or di(lower alkyl)amino groups, keto group, lower alkanoyl groups and the like. The lower alkyl moiety in the aforementioned substituents may have one or more kinds of these substituents. R is preferably an unsubstituted lower alkyl group, or an alkyl group substituted with one sulfonic acid group, and more preferably, ethyl group can be used.

The compounds of the present invention may sometimes have one or more asymmetric carbon atoms depending on the kind of substituents, and isomers such as optical isomers and diastereoisomers based on one or more asymmetric carbon atoms may sometimes exist. Any of such isomers, any mixtures of the isomers, racemates and the like falls within the scope of the present invention. In addition, when the compound of the present invention has an alkyl group having an acidic substituent as group "R", for example, sulfonic acid group and the like, the compound may sometimes form an intermolecular twitter ion without need of an anion species represented by $X^-$. It should be understood that such compounds also fall within the scope of the present invention. A compound which forms a twitter ion in the molecule may sometimes have reduced ionicity and fails to have sufficient water solubility. Accordingly, when an alkyl group having a sulfonic acid group or the like is used as R, the sulfonic acid group is desirably in the form of a metal salt such as sodium sulfonate. Examples of the combination of a metal ion which forms the metal salt and $X^-$ preferably include, for example, NaI, KI, NaCl and the like.

A preferred compound among those of the present invention includes, for example, 2-[7-(1,3-dihydro-1,1-dimethyl-3-ethylbenz[e]indolin-2-ylidene)-1,3,5-heptatrienyl]-1,1-dimethyl-3-[[6-[(1,3-thiazolidine-2-thione)-1-yl]-6-oxo] hexyl]-1H-benz[e]indolium chloride (herein sometimes referred to as "ICG-ATT"). However, the compound of the present invention is not limited to the aforementioned specific compound.

Methods for preparation of the compounds of the present invention are not particularly limited, and those prepared by any methods of preparation fall within the scope of the present invention. As an example of the preparation of the compound of the present invention, the preparation of ICG-ATT is shown in the scheme set out below. In addition, details of the preparation will be shown in Examples of the present specification. Accordingly, a person skilled in the art can easily prepare the compounds of the present invention which fall within the aforementioned formula (I) by referring to the following scheme and specific explanations in Examples, and appropriately choosing starting materials, reagents and reaction conditions, and if necessary, by adding appropriate alteration or modification to these methods (in the scheme, Et represents ethyl group; Me, methyl group; WSCD, 1-(3-dimethylaminopropyl)-3-ethylcarbodiimide hydrochloride; and, DMAP, dimethylaminopyridine).

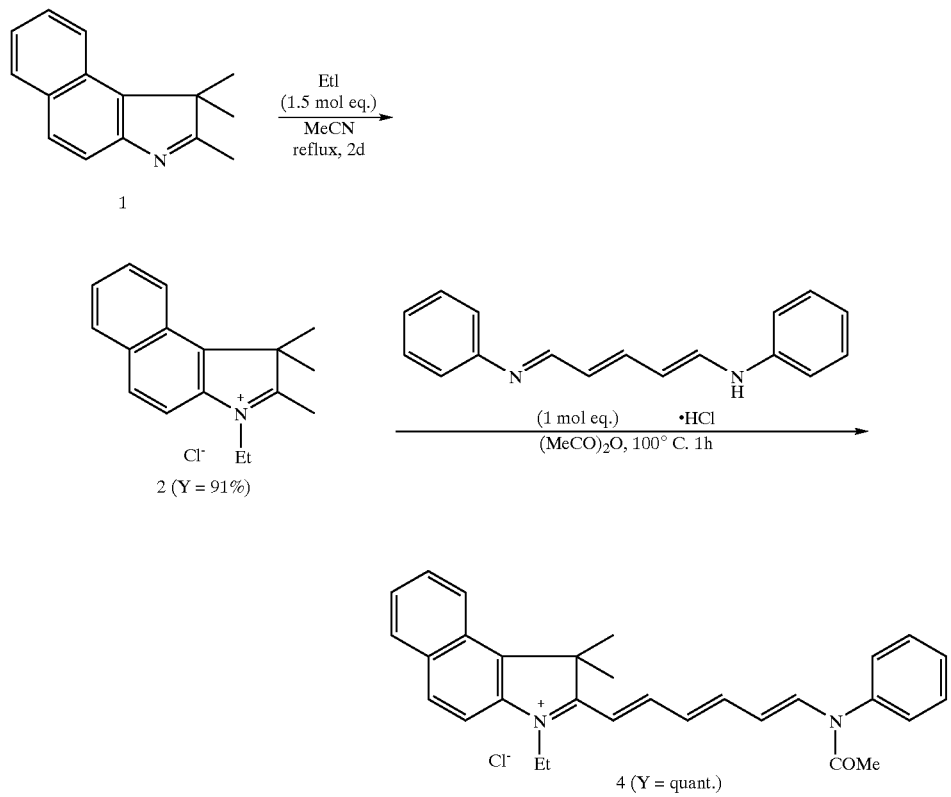

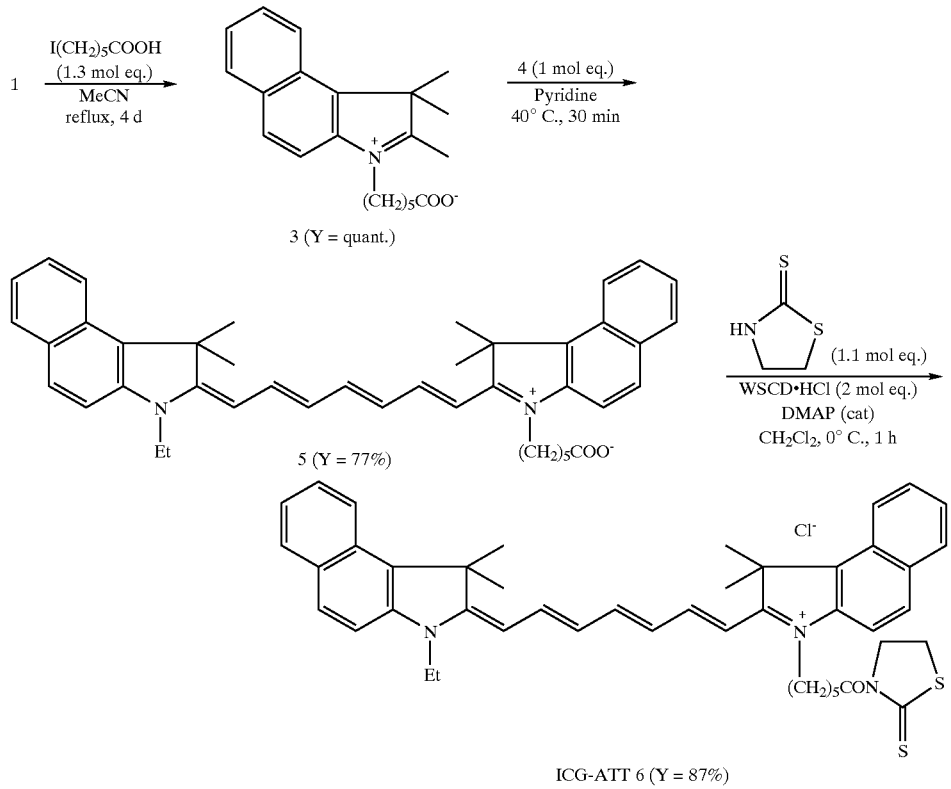

The compound of the present invention has properties that the compound is substantially non-fluorescent under the normal solar light or a fluorescent lamp, whilst the compound emits extremely strong fluorescence when being irradiated by the near infrared light. In addition, the compound of the present invention has excellent solubility in water, and is featured to react selectively and efficiently with amino group existing in amino acids, oligopeptides, proteins or the like to give acylated compounds. Accordingly, the compound of the present invention is useful as a fluorescent labeling agent for amino acids, oligopeptides, proteins, fats, saccharides and the like.

For example, the existence of cancer cells or cancer tissues can be verified by labeling an anti-tumor antibody with the compound of the present invention, and then allowing the labeled antibody to contact with a tissue or an organ. For diagnosis, a tissue section or the like may be fixed by an appropriate method such as the paraffin method and observed under a microscope. A living tissue can be immunochemically stained and observed with an endoscope. Recently, various fluorescence imaging methods using a near infrared fluorescent substance have been proposed (e.g., Japanese Patent Unexamined Publication (KOKAI) Hei. No. 9-309845; J. Neurosurg., 87, pp. 738–745, 1997; Medical Electron and Bioengineering (Iyodenshi to Seitaikogaku), 34, pp. 316–322, 1996 and the like), and the compound of the present invention can be utilized as a medicament for diagnosis utilizing the fluorescence imaging technique.

Moreover, a method of endoscopic treatment of an early gastric cancer by using a high power semiconductor laser with indocyanine green has been proposed (Gastroenterological Endoscopy, 39, 1753–1765, 1997; Gastroenterological Endoscopy, 39, 1766–1774, 1997). This method can elevate laser absorption in a tissue with the aid of indocyanine green and promote the heat clotting or transpiration of tissues, especially transpiration, and is expected to be useful for treatments of early cancers. The compound of the present invention can also be used for the aforementioned laser treatment. As the laser, high power semiconductor lasers in the near infrared region are suitable, and examples of a cancer to be treated include, for example, stomach cancer, esophageal carcinoma, duodenal carcinoma, rectum cancer and the like. Cancers curable by percutaneous endoscopic operations may also be treated.

When the compound of the present invention is used as a medicament for the aforementioned diagnosis or therapeutic treatment, the compound is preferably prepared in the form of a pharmaceutical composition by using one or more kinds of additives for pharmaceuticals. Pharmaceutical compositions in the form of a solid or a liquid or the like can be prepared, for example, by using appropriate additives for pharmaceuticals such as buffering agents, solubilizing aids, pH adjusters, excipients, antiseptics and the like. The form of the pharmaceutical composition suitable for diagnosis or therapeutic treatment and the preparation thereof can be appropriately chosen by a person skilled in the art. Uses of the compound of the present invention are hereinbefore specifically explained. However, the uses of the compound of the present invention are not limited to the aforementioned examples.

EXAMPLES

The present invention will be more specifically explained with reference to Examples. However, the scope of the present invention is not limited to the following Examples. In the following Examples, protein which is labeled with the compound of the present invention is sometimes referred to as ICG-protein (ICG-BSA, ICG-IgG).

Example 1
Preparation of the Compound of the Present Invention

All the melting points were measured with a Yanagimoto-Micro apparatus and were not corrected. Nuclear magnetic resonance ($^1$H-NMR) spectrum of a protein was recorded by using a spectrometer, JEOL-FX-200 or JEOL-GSX-400. Chemical shifts were indicated as δ values (ppm) using tetramethylsilane as the internal standard. The fast atom bombardment mass spectrometric analysis (FAB) or the electron ionization mass spectrometric analysis (EI) was performed by using a JEOL-SX-102A apparatus. The elemental analysis resulted in the values within ±0.4% of the theoretical values. The UV-vis spectrum was measured by using a Beckmann's 650-40 spectrometer. The fluorescence spectrum was recorded with a Hitachi's 650-40 luminescence spectrometer. The column chromatography was performed by using Merck's Silica Gel 60 (70–230 mesh). The compound numbers in Examples correspond to those in the aforementioned scheme.

1,1,2-Trimethyl-3-ethylbenz[e]indolium Iodide (2)

Ethyl iodide (1.1 g, 7.2 mmol) was added to an acetonitrile solution (40 ml) of 1,1,2-trimethylbenz[e]indole (1) (1.0 g, 4.8 mmol, Daiichi Pure Chemicals Co., Ltd.), and then the mixture was heated under reflux for 2 days. The reaction mixture was concentrated under reduced pressure, and ether (80 ml) was added to the residue. The resulting solid was repeatedly washed with ether to obtain the title compound (2) as a dark violet solid (1.6 g, 91%). mp. 213–218° C. (decomposition).

$^1$H-NMR (200 MHz, CD$_3$OD) δ1.7 (t, J=7.3 Hz, 2H), 1.9 (s, 6H), 3.2 (s, 3H), 4.9 (q, J=7.3 Hz, 2H), 7.6–8.2 (m, 6H).

HRFAB-MS m/z 238.1594 (calcd for C$_{17}$H$_{20}$N 238.1596) M$^+$-HI+H.

Anal. Calcd. for C$_{17}$H$_{20}$NI; C, 55.90; H, 3.83. Found: C, 55.67; H, 3.65.

1,1,2-Trimethyl-3-(6-carboxylatehexyl)benz[e]indolium Iodide (3)

6-Iodohexanoic acid (8.6 g, 35.4 mmol) was added an acetonitrile solution (240 ml) of 1,1,2-trimethylbenz[e]indole (1) (5.7 g, 27.2 mmol), and then the mixture was heated under reflux for 4 days. The reaction mixture was concentrated under reduced pressure, and ether (500 ml) was added to the residue. The resulting solid was repeatedly washed with ether to obtain the title compound (3) as a dark violet solid (9.8 g, quantitatively). mp. 220–224° C. (decomposition).

$^1$H-NMR (200 MHz, CD$_3$OD) δ1.6 (m, 2H), 1.7 (m, 2H), 1.8 (s, 6H), 2.1 (m, 2H), 2.4 (t, J=6.8 Hz, 2H), 3.3 (s, 3H), 4.6 (t, J=7.6 Hz, 2H), 7.7–7.9 (m, 2H), 8.0 (d, J=9.0 Hz, 1H), 8.1–8.4 (m, 3H).

HRFAB-MS m/z 324.1950 (calcd. for C$_{21}$H$_{26}$NO$_2$ 324.1964) M$^+$-H.

2-[6-(N-Phenyl-N-acetylamino)-1,3,5-heptatrienyl]-1,1-dimethyl-3-ethyl-1H-benz[e]indolium Chloride (4)

An acetic anhydride suspension (160 ml) of compound (2) (8.0 g, 22.0 mmol) and glutaconaldehyde dianil (6.3 g, 22.0 mmol) was heated to 100° C. for 1 hour. The reaction mixture was cooled and then poured into water (900 ml). The resulting solid was repeatedly washed with water to obtain the title compound (4) as a dark red solid (11.0 g, quantitatively). mp 165–168° C. (decomposition).

$^1$H-NMR (200 MHz, CDCl$_3$) δ1.6 (t, J=7.1 Hz, 3H), 1.97 (S, 3H), 2.00 (s, 6H), 4.8 (m, 2H), 5.4 (t, J=12.5 Hz, 1H), 6.9 (dd, J=9.8, 10.0 Hz, 1H), 7.1–8.3 (m, 15H).

HRFAB-MS m/z 435.2428 (calcd. for C$_{43}$H$_{31}$N$_2$O$_2$ 435.2436) M$^+$-HCl+H.

2-[7-(1,3-Dihydro-1,1-dimethyl-3-ethylbenz[e]indolin-2-ylidene)-1,3,5-heptatrienyl]-1,1-dimethyl-3-(6-carboxylatehexyl)-1H-benz[e]indolium Inner Additive Salt (5)

A pyridine solution (2 ml) of compound (3) (0.10 g, 0.31 mmol) and compound (4) (0.15 g, 0.31 mmol) was stirred at 40° C. for 30 minutes. The solvent was evaporated under reduced pressure, and then the residue was subjected to silica gel column chromatography and eluted with chloroform-methanol (100:1 to 10:1) to obtain the title compound (5) as a dark green solid (0.15 g, 77%). mp. 179–183° C. (decomposition).

$^1$H-NMR (200 MHz, CDCl$_3$) δ1.4 (t, J=6.8 Hz, 3H), 1.5–2.0 (m, 6H), 1.9 (s, 12H), 2.4 (t, J=6.6 Hz, 2H), 4.2 (m, 4H), 6.1 (d, J=13.4 Hz, 1H), 6.3 (d, J=13.7 Hz, 1H), 6.7 (t, J=12.7 Hz, 2H), 7.3–8.2 (m, 15H).

HRFAB-MS m/z 623.3641 (calcd. for C$_{43}$H$_{47}$N$_2$O$_2$ 623.3638) M$^+$+H.

2-[7-(1,3-Dihydro-1,1-dimethyl-3-ethylbenz[e]indolin-2-ylidene)-1,3,5-heptatrienyl]-1,1-dimethyl-3-[[6-[(1,3-thiazolidine-2-thion)-1-yl]-6-oxo]hexyl]-1H-benz[e]indolium Chloride (6)

1,3-Thiazolidine-2-thione (42 mg, 0.353 mmol), 1-(3-dimethylaminopropyl)-3-ethyl-carbodiimide hydrochloride (123 mg, 0.642 mmol), and 4-dimethylaminopyridine (4 mg, 0.032 mmol) were added to a dichloromethane solution (4 ml) of compound (5) (200 mg, 0.321 mmol) at 0° C. The reaction mixture was stirred at 0° C. for 1 hour, then added with 0.1 N HCl (10 ml), and extracted with chloroform (10 ml×3). The organic layer was washed with water, and concentrated under reduced pressure. The oily residue was subjected to silica gel column chromatography and eluted with chloroform-acetonitrile (30:1 to 4:1) to obtain the title compound (6) as a dark green solid (212 mg, 87%). mp. 158–161° C.

$^1$H-NMR (400 MHz, CDCl$_3$) δ1.5 (t, J=7.1 Hz, 3H), 1.2–2.1 (m, 6H), 2.0 (s, 12H), 3.28 (t, J=7.3 Hz, 2H), 3.34 (dd, J=7.3, 7.8 Hz, 2H), 4.1–4.4 (m, 4H), 4.6 (dd,J=7.3, 7.8 Hz, 2H), 6.3 (dd, J=12.7, 13.2 Hz, 2H), 6.7 (m, 2H), 7.3–8.2 (m, 15H).

HRFAB-MS m/z 724.3408 (calcd. for C$_{46}$H$_{50}$N$_3$OS$_2$ 724.3395) M$^+$+HCl+H. λ ex=765 nm, λ em=830 nm (DMF).

Example 2
Reaction of the Compound of the Present Invention with Various Reactive Functional Groups 2-[7-(1,3-Dihydro-1,1-dimethyl-3-ethylbenz[e]indolin-2-ylidene)-1,3,5-heptatrienyl]-1,1-dimethyl-3-[5-[N-(2-phenylethyl)aminocarbonyl]pentyl]-1H-benz[e]indolium Chloride (7)

To an acetonitrile solution (2.5 ml) of compound (6) (94 mg, 0.124 mmol), 2-phenylethylamine (30 mg, 0.247 mmol)

was added at 0° C. The reaction mixture was stirred at 0° C. for 30 minutes, then poured into 1 N HCl, and extracted with chloroform (10 ml×3), and the organic layer was washed with water (10 ml). The solvent was evaporated under reduced pressure, and the residue was subjected to gel filtration chromatography with a Sephadex LH-20 (1.5×50 cm) column and eluted with methanol to obtain the title compound (7) as a dark green solid (85 mg, 91%). mp. 132–135° C.

$^1$H-NMR (200 MHz, CDCl$_3$) δ1.5 (t, J=7.1 Hz, 3H), 1.2–2.2 (m, 18H), 2.4 (t, J=7.1 Hz, 2H), 2.9 (dd, J=7.1, 8.3 Hz, 2H), 3.5 (dd, J=6.6, 8.3 Hz, 2H), 4.0–4.3 (m, 4H), 6.1 (d, J=13.4 Hz, 1H), 6.3 (d, J=13.7 Hz, 1H), 6.5–6.8 (m, 2H), 7.1–8.2 (m, 20H).

HRFAB-MS m/z 726.4408 (calcd. for C$_{51}$H$_{56}$N$_2$O 726.4423) M$^+$-HCl+H.

To an acetonitrile solution (2.5 ml) of compound (6) (29 mg, 0.038 mmol), 2-phenylethyl alcohol (9.6 mg, 0.077 mmol) was added at 0° C. The reaction mixture was stirred at 0° C. for 30 minutes and then at room temperature for 30 minutes, then poured into 1 N HCl. The mixture was extracted with chloroform (10 ml×3), and the organic layer was washed with water (10 ml). The solvent was evaporated under reduced pressure to obtain an oily residue. The residue was subjected to silica gel column chromatography and eluted with chloroform-methanol(100:1 to 4:1) to recover 96% of compound (6) as a dark green solid. Similarly, compound (6) (30 mg, 0.040 mmol) was treated with 2-phenylethylthiol (11.1 mg, 0.079 mmol) to recover 96% of compound (6) (29 mg). These results indicate that the compound of the present invention does not react with hydroxyl group or thiol group, and has extremely high reactivity to amino group, and that the compound of the present invention is a chemically selective labeling agent to an amino group similar to the conventional ATT (Nagao, Y. et al., Heterocycles, 1982, 17, 537).

Example 3
Reaction of the Compound of the Present Invention with Basic Amino Acid Derivatives N-ε-[6-[2-[7-(1,3-Dihydro-1,1-dimethyl-3-ethylbenz[e]indolin-2-ylidene)-1,3,5-heptatrienyl]-1,1-dimethyl-1H-benz[e]indolium-3-yl]hexaneamide]-N-α-acetyl-L-lysine Methyl Ester Chloride (8)

An aqueous solution (0.5 ml) of N-α-acetyl-L-lysine methyl ester hydrochloride (35 mg, 0.147 mmol) and triethylamine (15 mg, 0.147 mmol) were added to an acetonitrile solution (20 ml) of compound (6) (56 mg, 0.074 mmol) at 0° C. The reaction mixture was stirred at 0° C. for 30 minutes, then poured into 1 N HCl (10 ml). The mixture was extracted with chloroform (10 ml×3), and then the organic phase was washed with water (10 ml). The solvent was evaporated under reduced pressure, and then the residue was subjected to gel filtration chromatography with a Sephadex LH-20 (2.0×50 cm) column and eluted with methanol to obtain the title compound (8) as a dark green solid (54 mg, 86%). mp. 126–129° C.

$^1$H-NMR (200 MHz, CDCl$_3$) δ0.8–2.0 (m, 27H), 2.1 (s, 3H), 2.5 (t, J=6.7 Hz, 2H), 3.2–3.4 (m, 2H), 3.7 (s, 3H), 4.1–4.3 (m, 4H), 4.4–4.5 (m, 1H), 6.1 (d, J=13.4 Hz, 1H), 6.4 (d, J=13.7 Hz, 1H), 6.6 (dd, J=12.2, 12.7 Hz, 1H), 6.9 (dd, J=10.3, 13.2 Hz, 1H), 7.1–8.2 (m, 15H).

HRFAB-MS m/z 807.4827 (calcd. for C$_{52}$H$_{63}$N$_4$O$_4$ 807.4849) M$^+$-HCl+H.

N-ε-[6-[2-[7-(1,3-Dihydro-1,1-dimethyl-3-ethylbenz[e]indolin-2-ylidene)-1,3,5-heptatrienyl]-1,1-dimethyl-1H-benz[e]indolium-3-yl]hexaneamide]-N-α-benzyloxy-carbonyl-L-lysine Methyl Ester Chloride (9)

The title compound (9) was prepared in a similar manner to the above and obtained as a dark green solid (89%). mp. 142–144° C.

$^1$H-NMR (200 MHz, CDCl$_3$) δ1.2–2.2 (m, 27H), 2.4 (t, J=6.7 Hz, 2H), 3.2 (m, 2h), 3.7 (s, 3H), 4.0–4.4 (m, 5H), 5.1 (s, 2H), 5.7 (d, J=7.6 Hz, 1H), 6.1 (d, J=13.4 Hz, 1H), 6.4 (d, J=13.2 Hz, 1H), 6.5–6.9 (m, 2H), 7.1–8.2 (m, 19H).

HRFAB-MS m/z 899.5142 (calcd. for C$_{58}$H$_{67}$N$_4$O$_5$ 899.5111) M$^+$-HCl+H.

N-[6-[2-[7-(1,3-Dihydro-1,1-dimethyl-3-ethylbenz[e]indolin-2-ylidene)-1,3,5-heptatrienyl]-1,1-dimethyl-1H-benz[e]indolium-3-yl]hexaneamide]-glycine Ethyl Ester Chloride (10)

The title compound (10) was prepared in a similar manner to the above and obtained as a dark green solid (82%). mp. 145–150° C.

$^1$H-NMR (200 MHz, CDCl$_3$) δ1.3 (t, J=7.1 Hz, 3H), 1.4–2.2 (m, 21H), 2.4 (t, J=6.7 Hz, 2H), 4.0–4.4 (m, 8H), 6.1–7.1 (m, 4H), 7.2-8.2 (m, 15H).

HRFAB-MS m/z 704.4165 (calcd. for C$_{47}$H$_{54}$N$_3$O$_3$ 708.4177) M$^+$-HCl+H.

The results of reactions carried out in similar manners under various conditions are shown in Table 1. The amino groups of protected lysine and protected glycine derivatives reacted with the compound of the present invention under mild conditions to give the corresponding amide compounds (8 to 10) in good yields as shown in the table. The acylation efficiently progressed at 0° C. or room temperature even in an aqueous solution of acetonitrile or an aqueous solution of tetrahydrofuran. These results indicate that the compound of the present invention can efficiently label amino groups derived from amino acid residues in oligopeptides or proteins (in the table, "a" indicates yields after isolation, and "b" indicates a yield determined by $^1$H-NMR.).

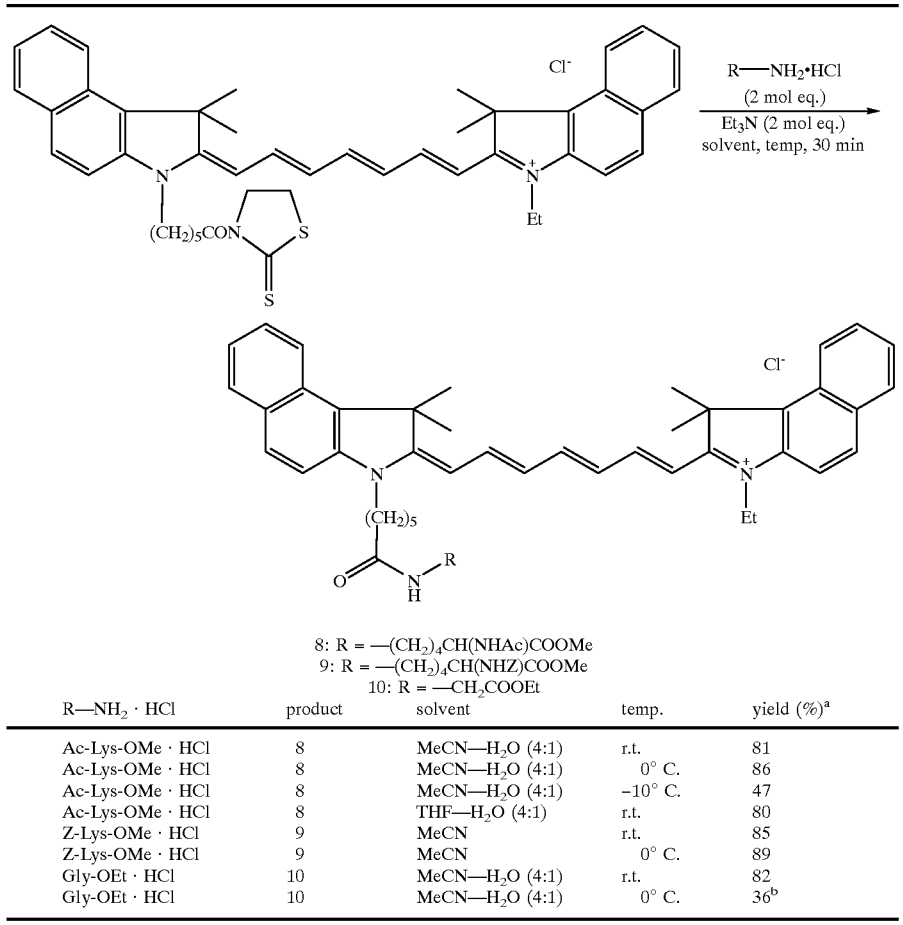

| R—NH$_2$ · HCl | product | solvent | temp. | yield (%)$^a$ |
|---|---|---|---|---|
| Ac-Lys-OMe · HCl | 8 | MeCN—H$_2$O (4:1) | r.t. | 81 |
| Ac-Lys-OMe · HCl | 8 | MeCN—H$_2$O (4:1) | 0° C. | 86 |
| Ac-Lys-OMe · HCl | 8 | MeCN—H$_2$O (4:1) | −10° C. | 47 |
| Ac-Lys-OMe · HCl | 8 | THF—H$_2$O (4:1) | r.t. | 80 |
| Z-Lys-OMe · HCl | 9 | MeCN | r.t. | 85 |
| Z-Lys-OMe · HCl | 9 | MeCN | 0° C. | 89 |
| Gly-OEt · HCl | 10 | MeCN—H$_2$O (4:1) | r.t. | 82 |
| Gly-OEt · HCl | 10 | MeCN—H$_2$O (4:1) | 0° C. | 36$^b$ |

Example 4
Labeling of a Protein by Using the Compound of the Present Invention

A DMF solution (250 μl) of compound (6) of the present invention obtained in Example 1 (3.7 μmol/ml) was added to a 0.1 M phosphate buffer solution (pH 7.5, 1 ml) of BSA (2 mg). The reaction mixture was allowed to stand for 30 minutes and subjected to Sephadex LH-20 column chromatography (1.5 cm×50 cm), and then eluted with a 0.1 M phosphate buffer solution (pH 7.5) to obtain a fraction of ICG-labeled protein. For IgG (2 mg), the labeling reaction with a DMF solution (250 μl) of ICG-ATT (6) (3.7 μmol/ml) was carried out in a similar manner to the above by using 0.1 M carbonate buffer (pH 9.5) instead of 0.1 M phosphate buffer (pH 7.5). The 0.1 M phosphate or the carbonate buffer solution (1 ml), containing the ICG-labeled protein (BSA or IgG) obtained by the Sephadex LH-20 column chromatography, was added to ethyl acetate (1 ml), and the mixture was vigorously stirred for 30 minutes to remove fluorescent compounds which bound to the protein through noncovalent bond. Then, the aqueous layer containing the labeled protein and the ethyl acetate layer were subjected to UV-vis and fluorescence analyses.

As a result, the ratios of the fluorescent substance in the aqueous layer and the ethyl acetate layer were 44% in BSA and 69% in IgG. The protein concentration in the labeled protein was measured by using a protein assay kit (Bio-Rad, CA), and the total ICG concentration in the labeled protein was determined from the absorbance (789 nm) of the DMF solution and the ε value of the ICD derivative. The ratios of ICG versus protein (ICG/protein) in each ICG-labeled protein were 21.5 (BSA) and 23.6 (IgG). The absorption and fluorescence properties of ICG-ATT (6), ICG-BSA and ICG-IgG are shown in Table 2. It is proved that λmax, λex, and λem of these compounds are in the near infrared region. From the foregoing results, it is readily understood that the compounds of the present invention are useful as near infrared fluorescent labeling agents for proteins and oligopeptides.

| | UV-vis | fluorescent | |
|---|---|---|---|
| compd. | abs (λmax) | λex | λem |
| ICG-ATT (6) | 789 nm | 765 nm | 830 nm |
| ICG-BSA (12, 13) | 789 nm | 766 nm | 828 nm |
| ICG-IgG (12, 13) | 789 nm | 765 nm | 826 nm |

Industrial Applicability

The compounds of the present invention can emit strong fluorescence in the near infrared region and can selectively label amino groups of amino acid residues in proteins and oligopeptides. Accordingly, the compounds are useful for fluorescent labeling agents and medicaments for diagnosis by means of tissue immunochemical dyeing.

What is claimed is:

1. A compound represented by the following formula (I):

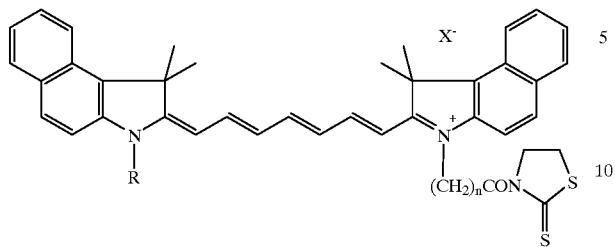

wherein R represents a lower alkyl group which may be substituted; n represents an integer of from 1 to 10; and X represents an anion species.

2. The compound according to claim 1 wherein R is a $C_{1-6}$ alkyl group and n is 5.

3. The compound according to claim 1 which is 2-[7-(1,3-dihydro-1,1-dimethyl-3-ethylbenz[e]indolin-2-ylidene)-1,3,5-heptatrienyl]-1,1-dimethyl-3-[[6-[(1,3-thiazolidine-2-thion)-1-yl]-6-oxo]hexyl]-1H-benz[e]indolium chloride.

4. A fluorescent labeling agent which comprises the compound according to claim 1.

5. A medicament for diagnosis which comprises the compound according to claim 1.

6. A medicament for therapeutic treatment of a cancer by means of a laser which comprises the compound according to claim 1.

* * * * *